United States Patent [19]
Daly

[11] Patent Number: 5,042,084
[45] Date of Patent: Aug. 20, 1991

[54] THREE WIRE SYSTEM FOR COCHLEAR IMPLANT PROCESSOR

[75] Inventor: Christopher Daly, Bilgola Plateau, Australia

[73] Assignee: Cochlear Pty. Limited, Australia

[21] Appl. No.: 404,230

[22] Filed: Sep. 7, 1989

[51] Int. Cl.$^5$ .......................... H04B 5/00; A61N 1/00
[52] U.S. Cl. ...................................... 455/41; 455/66; 381/68; 128/419 R; 128/421
[58] Field of Search ...................... 455/41, 63, 66, 295, 455/296, 107; 128/419 PG, 419 R, 420.5, 420.6, 421; 379/55; 381/68, 68.6, 69; 333/12, 181, 182, 236; 174/32; 307/89–90

[56] References Cited

U.S. PATENT DOCUMENTS

| | | | |
|---|---|---|---|
| 3,568,109 | 3/1971 | Nevens | 333/182 |
| 3,638,147 | 1/1972 | Denes | 333/182 |
| 3,665,315 | 5/1972 | Glatzer et al. | 455/107 |
| 4,441,210 | 4/1984 | Hochmair et al. | 455/41 |
| 4,532,231 | 8/1985 | Crosby et al. | 128/419 |
| 4,654,880 | 3/1987 | Sontag | 455/41 |
| 4,918,745 | 4/1990 | Hutchinson | 455/41 |
| 4,952,896 | 8/1990 | Dawson Jr. | 333/182 |

OTHER PUBLICATIONS

Donaldson, P. E. K., "Three Separation-Insensitive Radiofrequency Inductive Links", J. Med. Eng. & Tech., vol. 11, No. 1, Jan./Feb. 1987, pp. 23–29.
Raab, F. H. et al., "Transistor Power Losses in the Class E Tuned Power Amplifier" IEEE J of S. S. Cirs. vol. SC-13, N. 6, Dec. 1978, pp. 912–914.
Molnar, B. "Basic Limitation on Waveforms Achievable in Single-Ended Switching Mode Tuned (Class E) Power Amplifiers", IEEE J. S. S. Cirs. vol. SC-19, No. 1. Feb. 1984, pp. 144–146.
Galbraith, D. C., "A Wide-Band Efficient Inductive Transdermal Power and Data Link with Coupling Insensitive Gain", IEEE Trans. Biomed Eng. vol. BME-34, No. 4, Apr., 1987, pp. 265–275.

*Primary Examiner*—Reinhard J. Eisenzopf
*Assistant Examiner*—Andrew Faile
*Attorney, Agent, or Firm*—Gottlieb, Rackman & Reisman

[57] ABSTRACT

A transmission system wherein a transmitter includes a first tuned circuit and a transmitter coil is part of a second tuned circuit. A coupling means couples energy between the first tuned circuit and the second tuned circuit. A three wire unshielded cable carries both radio frequency and audio frequency signals. Filter means are provided for filtering the audio frequency signal so that it is free of interference from the radio frequency signal, which may include audio components due to its generally pulsed nature. The circuit may be adjusted for relatively constant coupling to a receiving coil as separation between the transmitter coil and the receiving coil changes.

16 Claims, 3 Drawing Sheets

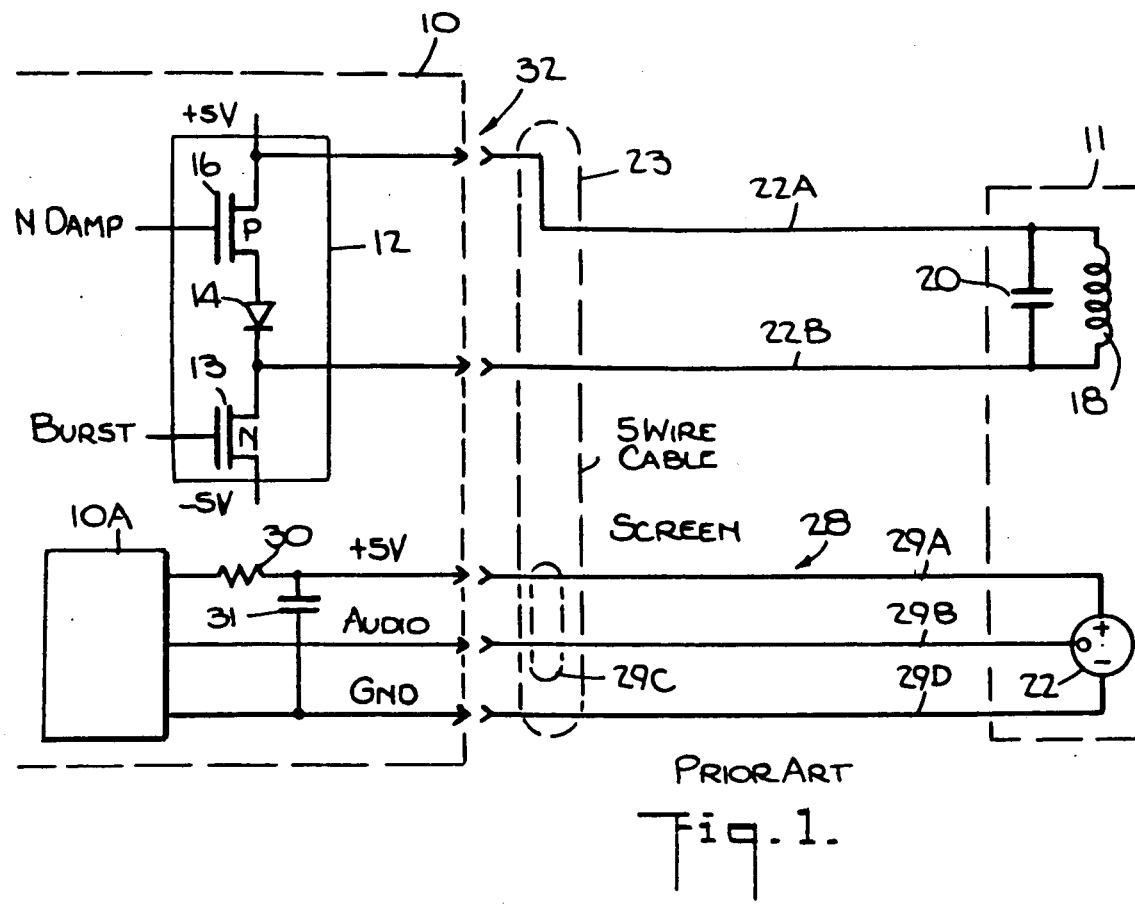
PRIOR ART
Fig. 1.
Fig. 2A.
BURST
N DAMP
Fig. 2B.
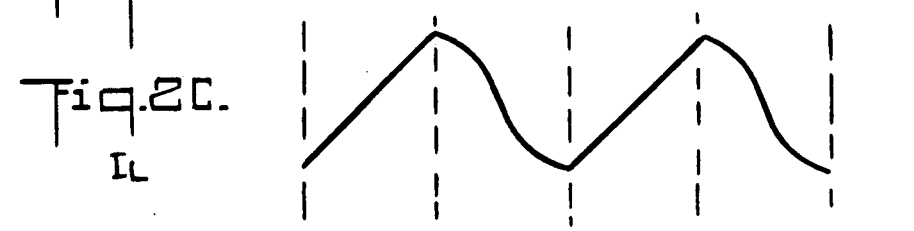
Fig. 2C.
$I_L$
Fig. 2D.
$V_L$ +5
−5

THREE WIRE SYSTEM FOR COCHLEAR IMPLANT PROCESSOR

TECHNICAL FIELD

This invention relates to the field of signal transmission for cochlear implant systems. More particularly it relates to a system for transmitting both audio and radio frequency energy in a multiconductor cable.

BACKGROUND OF THE INVENTION

The speech processor for the cochlear implant is a body worn device which receives audio signals from an ear level microphone and transmits an encoded RF signal to the implanted device via a coil located over the implant site. Thus, there is a requirement to transfer a low level audio signal (typically 1 millivolt RMS) from the microphone to the speech processor and a high level signal (approximately 10 volts RMS) back to the coil. This represents an amplitude difference of 80 dB.

The high level signal is generally a wide band burst modulated RF carrier where the bursts are encoded stimulus data. Typically, the burst modulated carrier includes frequency components in the audio frequency range. The low level signal is an audio signal with a bandwidth of interest of 100 Hz to 10 KHz. The high level RF signal, if burst width modulated, has significant frequency components within the audio spectrum. It is therefore necessary to take special precautions to minimize crosstalk between the two signals. In the past this has been achieved by the use of a custom made multicore screened cable, which provided independently shielded conductors for the microphone connections and lower capacitance conductors for the transmitter coil connections. While this achieves the necessary isolation between the two signals, it requires a special cable which is heavier than ideal and very expensive to manufacture and to terminate to connectors.

Body worn hearing aids have made use of a light weight three wire twisted cable which is both readily available able and inexpensive. Several manufacturers provide standard length cables terminated with standardized three pin IEC plugs. These cables are relatively low in capacitance, but are not screened. However, because of the abovementioned crosstalk difficulties, the audio and RF circuits used in prior art cochlear implant systems cannot utilize only three unshielded conductors.

FIG. 1, illustrates a prior art five wire system for connection of a processor 10 having an audio signal processing circuit 10A to a headset 11. An RF transmitter 12, within processor 10, operates in class-E mode, i.e. the driver transistor 13, which is connected in series with a diode 14 and a damping transistor 16, conducts for approximately fifty percent of the total cycle and switches when the voltage across it is close to zero. A transmitter coil 18 and a capacitor 20 form a tuned circuit, which is connected to transmitter 12 by conductors 22A and 22B of five wire cable 23.

A microphone 22 is connected to audio signal processing circuit 10A of processor 10 via an independently shielded three wire portion 28 of cable 23. Cable 23 includes a power conductor 29A and audio conductor 29B, shielded by a braid 29C connected to a ground conductor 29D. A D.C. bias supply is filtered by a resistor 30 and a capacitor 31 to minimize noise of power supply origin. A five wire connector 32, which is generally fairly expensive, is used to connect cable 23 to processor 10.

The waveforms associated with the circuit of FIG. 1 are illustrated in FIGS. 2A to 2D. The BURST waveform of FIG. 2A is applied to the gate of transistor 13. The NDAMP waveform of FIG. 2B (the logical opposite of a damp waveform) is applied to the gate of transistor 16.

As illustrated in FIG. 2C, during the cycle, current in coil 18 changes approximately linearly from a peak negative value to a peak positive value. During the half cycle in which transistor 13 is turned off, current cycles sinusoidaly from a peak positive value back to a peak negative value. As illustrated in FIG. 2D, the voltage waveform across the wires 22A and 22B and coil 18 is asymmetrical, swinging from $-5$ volts to $+25$ Volts around the $+5$ volt supply, during the on and off times, respectively, of driver transistor 13. This extreme asymmetry in coil drive waveform results in significant low frequency components which are readily coupled into the audio signal processing circuit 10A.

The mutual coupling between transmitter coil 18 and a receiver coil (not shown in FIG. 1) increases as the distance between them decreases. The load across transmitter coil 18 increases accordingly, and this results in increased power to the transmitter. Ideally, the power consumption should decrease as the coupling increases. As illustrated in FIG. 3, the five wire system of FIG. 1, which uses the transmitter coil as the inductor in the class-E stage, exhibits characteristics opposite the ideal, whereby closer coupling reflects a lower impedance across the coil. This results in more energy being taken from the tuned circuit and consequently the transmitter draws more power.

Another disadvantage of the five wire system illustrated in FIG. 1 is that it is necessary to have a $+/-5$ volt power supply. Such a dual voltage power supply adds considerable cost to the system.

Prior attempts to achieve better efficiency have used stagger tuning of the transmitter and a receiver using a fixed transmitter frequency, or a self oscillating transmitter circuit which detunes as coupling coefficient increases. This latter approach is not usable with a fixed frequency transmitter which is preferred for the encoded pulsatile stimulation strategy.

SUMMARY OF THE INVENTION

It is an object of this invention to use a three wire twisted cable, of the type used with hearing aids, to transfer both low level audio signals and high level modulated RF signals with minimum crosstalk.

It is another object of this invention to improve the efficiency of energy transfer from the external transmitter system to an implanted receiver stimulator.

It is still another object of this invention to achieve operation of the transmitter circuit from a single voltage supply.

In accordance with the invention, a transmission system for transmitting audio and radio frequency energy comprises a three-wire unshielded cable; a radio frequency source connected to a first wire and second wire of the three wire cable; an audio frequency source connected to the second wire and a third wire of the three wire cable; and radio frequency filter means for filtering audio from the audio source to reduce interference from the radio frequency source. The filter means is disposed at least one end of the cable, and is preferably a pi network at each end. Radio frequency energy from the radio frequency source is at a voltage level several orders of magnitude higher than the voltage from the audio frequency source. The radio frequency source is preferably a pulsed and damped transmitter. The transmitter preferably includes a class-E amplifier to enhance efficiency.

In accordance with the invention, the transmission system finds application in a cochlear implant speech processor wherein the audio source is a microphone for receiving ambient audio. The microphone and a transmitter coil associated with the transmitter are located proximate to one another. The three wire unshielded cable has a first end and a second end. A radio frequency transmitter circuit is connected to a first wire and a second wire of the three wire cable at a first end thereof. A radio frequency transmitter coil is coupled to the first wire and the second wire of the three wire cable at the second end thereof. The audio frequency source, which is a microphone, is coupled to the second and third wires of the three wire cable at the second end thereof. An audio frequency processing means for processing audio from the audio frequency source is coupled to the second wire and the third wire of the cable at the first end thereof. A filter means for filtering the audio frequency energy from the microphone so that it is essentially free of radio frequency energy from the radio frequency transmitter circuit is provided.

The invention also contemplates a radio frequency transmission system having a transmitter with a first tuned circuit, a transmitter coil which is part of a second tuned circuit, and coupling means for coupling radio frequency energy from the first tuned circuit to the second tuned circuit. The coupling means may include a capacitor. The first tuned circuit includes a coil which may have a tap. The radio frequency driver, which includes at least one active device, connects to the coil at its end or at a tap, depending on the power level required and the supply voltage. One side of a capacitor coupling means is connected to one side of the coil and the other side is connected to the second tuned circuit.

In a radio frequency transmission system having a transmitter with a first resonant circuit, a transmitter coil which is part of a second resonant circuit separate and apart from the first resonant circuit and coupling means for coupling energy between the first resonant circuit and the second resonant circuit, the invention also contemplates a method for adjusting the power transferred to a receiving coil. The method comprises the steps of placing the transmitter coil at a minimum separation from the receiving coil; adjusting for resonance in the first resonant circuit so that the transmitter draws minimum power; separating the transmitter coil and the receiving coil to a maximum separation; and adjusting the coupling means to couple sufficient energy for reliable transmission to occur at the maximum separation. This procedure may be used iteratively to achieve optimum performance.

Preferably, the step of adjusting for resonance in the first resonant circuit is accomplished by adjusting a value of a capacitor. The coupling means is also a capacitor and the step of adjusting the coupling means comprises changing a value of that capacitor. The step of separating the transmitter coil and the receiver coil to a maximum separation comprises separation to a maximum distance or to a maximum misalignment.

The receiver coil is associated with a cochlear implant while the transmitter coil is associated with a cochlear speech processor. In the step of placing the receiver coil, the minimum distance is defined by placing the transmitter coil coaxially over the receiver coil.

BRIEF DESCRIPTION OF THE DRAWINGS

Further objects, features and advantages of the invention will become apparent upon consideration of the following detailed description in conjunction with the drawings in which:

FIG. 1 is a schematic diagram of a prior art five wire transmission system;

FIGS. 2A to 2D are timing diagrams of waveforms associated with the circuit of FIG. 1;

DESCRIPTION OF THE PREFERRED EMBODIMENT

Figure 4:
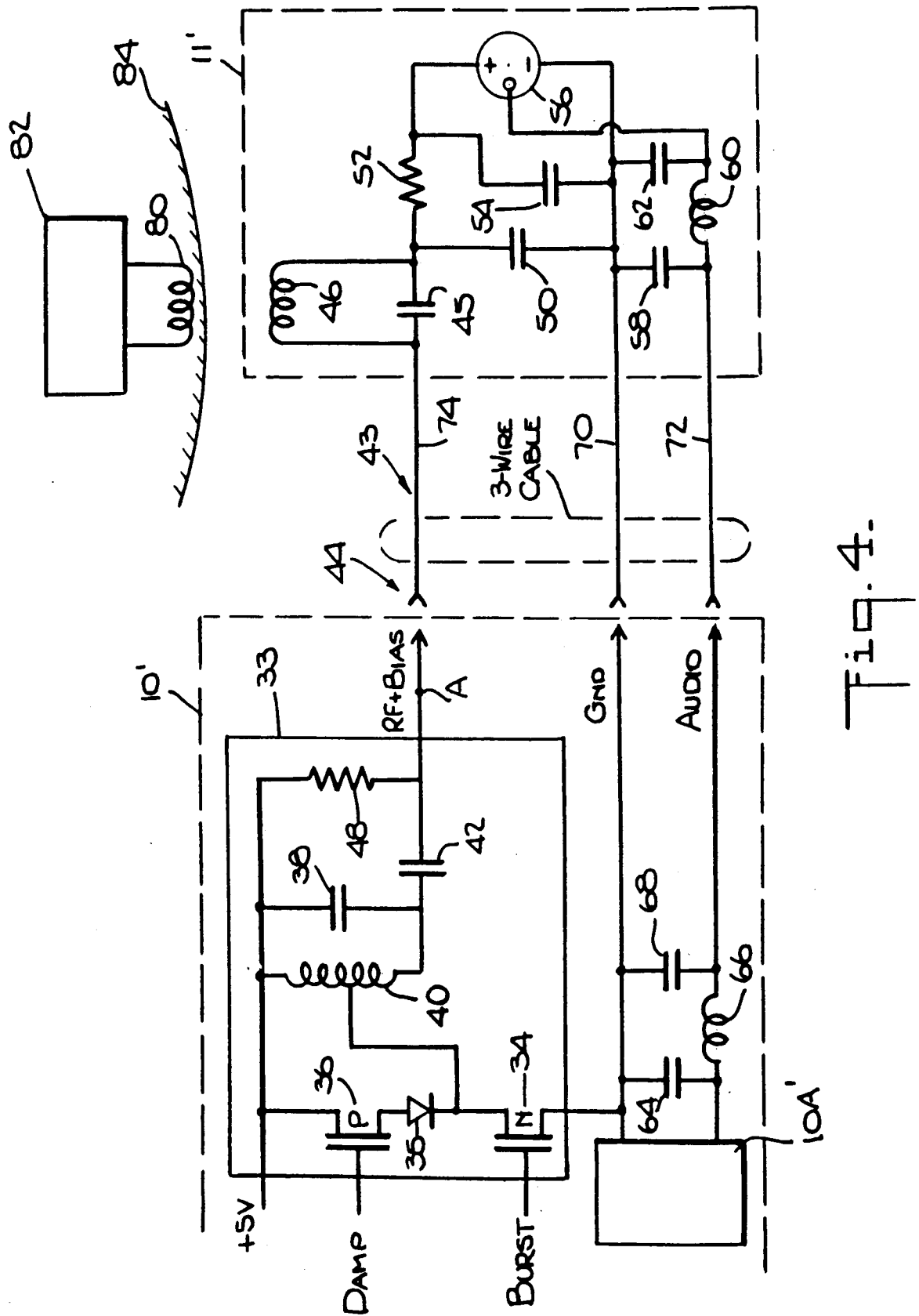
FIG. 4 is a schematic diagram of a three wire transmission system in accordance with the invention.

Referring to FIG. 4, a transmission system in accordance with the invention includes a speech processor 10' and a headset 11'. Speech processor 10' includes a transmitter circuit 33 and an audio signal processing circuit 10A'. Transmitter circuit 33 includes a driver transistor 34, a diode 35, and a damping transistor 36. Transistor 34 is an N-channel enhancement mode MOSFET with an on-resistance preferably less than five ohms for efficient operation of the transmitter. Transistor 36 is a P-channel enhancement mode MOSFET with an on-resistance of less than ten ohms. Both transistors have threshold voltages of less than 2.5 volts and can be driven directly from typical output drives of CMOS integrated circuits. They should have a voltage rating of at least 60 volts. Typical industry parts for transistors 34 and 36 are VN0610L and VP0610L, respectively.

Transmitter circuit 33 is of class-E design and operates with its own tuned circuit including a capacitor 38 and an inductor 40, the output of which is capacitively coupled by capacitor 42 to a three wire cable 43 (by a three pin electrical connector 44) and a tuned transmitter circuit including capacitor 45 and coil 46. Capacitor 45 must have a high quality dielectric, such as that of an NPO type capacitor. The tuned circuits are close to resonance at the transmission frequency, which in the preferred embodiment is at 2.5 MHz.

The voltage and current waveforms at drive transistor 34 are of the same form as those for the previously described five wire system illustrated in FIGS. 2A to 2D. Tuned inductor 40 is tapped to provide the necessary voltage gain and impedance transformation to drive transmitter coil 46. This is not an intrinsic feature of the design, but is necessary in order to achieve adequate power output to a prior existing transmitter coil, when operating from a single +5 volt supply, instead of the prior +/−5 volt supply. If a +/−5 volt supply, or a 10 volt supply, is available, it may not be necessary to provide a tap on the inductor.

A resistor 48 performs two functions:
a) it adds a +5V DC bias to the RF signal which enables a bias current to be derived for the microphone as more fully described below, and
b) it increases the effective damping to control the ringing of the transmitter circuit.

The effectiveness of diode 35 and transistor 36 on damping is reduced due to inductor 40 being tapped. When data is encoded as the number of cycles in a burst, excessive ringing can cause errors.

Cable 43 should have a capacitance of approximately 120 pF (typically +/−40 pF) as measured from one conductor to the other two conductors connected together. It is desirable that cable capacitance represents only a small proportion of the total tuning capacitance. This must be controlled within the stated range, as it forms part of the tuning capacitance for transmitter coil 46.

Cable 43 is preferably approximately 80 cm long to suit most individuals, and to allow the speech processor to be worn on a belt while the microphone is at ear level. It may be necessary to adjust the value of capacitor 45 to compensate for changes in capacitance when shorter or longer cables are used.

The resistance of each conductor of cable 43 should be as low as practical and typically less than two ohms. Losses become significant for lengths in excess of 1.5 meters, due to the non-ideal nature of the cable.

The voltage at point A consists of a radio frequency component and a bias voltage. It is a symmetrical sinusoidal signal with a 5 volt DC offset. The DC bias passes through coil 46 and is smoothed by the combined effect of resistor 48, a capacitor 50, a resistor 52, and an additional capacitor 54. The microphone 56, which is preferably a sensitive electret device of the type used in hearing aids, requires a bias voltage of between 0.9 and 20 volts and draws between 25 and 50 microamperes. If another type of microphone is used, it may be necessary to adjust the values of resistor 48 and resistor 52.

The power supply rejection of the microphone is quite low (on the order of approximately 5:1). The bias voltage noise must therefore be reduced to less than 10 microvolts RMS across the audio band, in order to achieve an acceptable input noise level. It is also necessary to prevent injection of RF energy into the microphone output, since this could be demodulated and appear as audio noise.

A capacitor 58, an inductor 60 and a capacitor 62 form a pi filter network which prevents RF injection to the output terminal of the microphone. An identical pi filter network including a capacitor 64, an inductor 66, and a capacitor 68 is used at the other end of cable 43 to prevent RF injection into the audio signal processing circuit 10A'. In this way, the relatively high level of RF signal coupled onto the audio line of the three-wire cable is attenuated to an insignificant level at the microphone and at the input of the processing circuit.

Electret microphone 56 has an output impedance of approximately 3000 ohms. Therefore the total capacitive loading must be limited to avoid degradation of the high frequency response of the microphone. Only frequencies of up to 6 KHz are of interest.

The effect of inductors 60 and 66 can be ignored at audio frequencies. If the cable capacitance is approximately 100 pF, the total capacitance of the cable and capacitors 58, 62, 64 and 68 is approximately 2.82 nF, which reduces the audio output of the microphone by less than 2.5 dB at 6 KHz.

Inductors 60 and 66 are chosen to be the highest value available in miniature chip inductors with the additional constraint that the self resonant frequency is above 2.5 MHz. The impedance of inductors 60 and 66 at 2.5 MHz is 7.38 Kohms. The impedance of a 680 pF capacitor at 2.5 MHz is 93.7 ohms.

The radio frequency voltage coupled onto the audio line of three wire cable 43 is minimized by the low impedance of the parallel combination of capacitors 58 and 62 and the capacitance between ground wire 70 and audio signal wire 72, when compared to the inter-cable capacitance to RF line 74. The residual RF voltage is then attenuated both into the microphone by inductor 60 and capacitor 62, and into the speech processing circuit 10A' by inductor 66 and capacitor 64, by a total of approximately 38 dB.

Typical values for the components used in the schematic diagram of FIG. 4 are:

| Capacitor 38 | 68 pf |
| --- | --- |
| Capacitor 42 | 56 pf |
| Capacitor 45 | 680 pf |
| Capacitor 50 | 0.1 uf |
| Capacitor 54 | 6.8 uf |
| Capacitors 58, 62, 64 and 68 | 680 pf |
| Inductors 60 and 66 | 470 uH |
| Resistor 48 | 4.7 Kohms |
| Resistor 52 | 4.7 Kohms |

Figure 5:
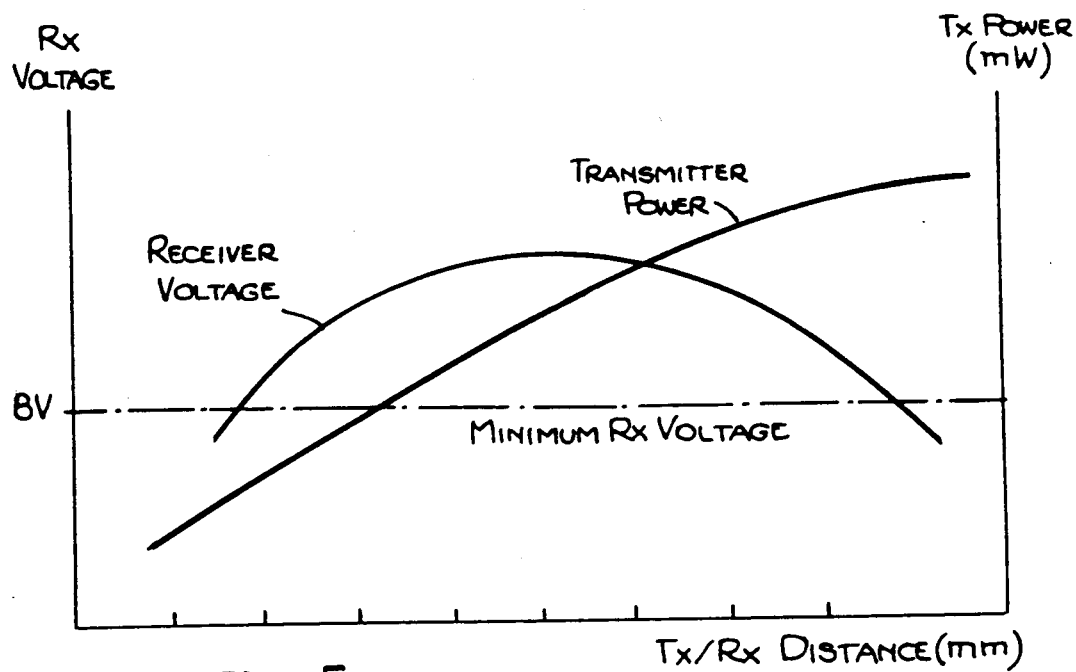
FIG. 5 is a graph of the coupling performance of a system in accordance with the invention as illustrated in FIG. 4.
Figure 3:
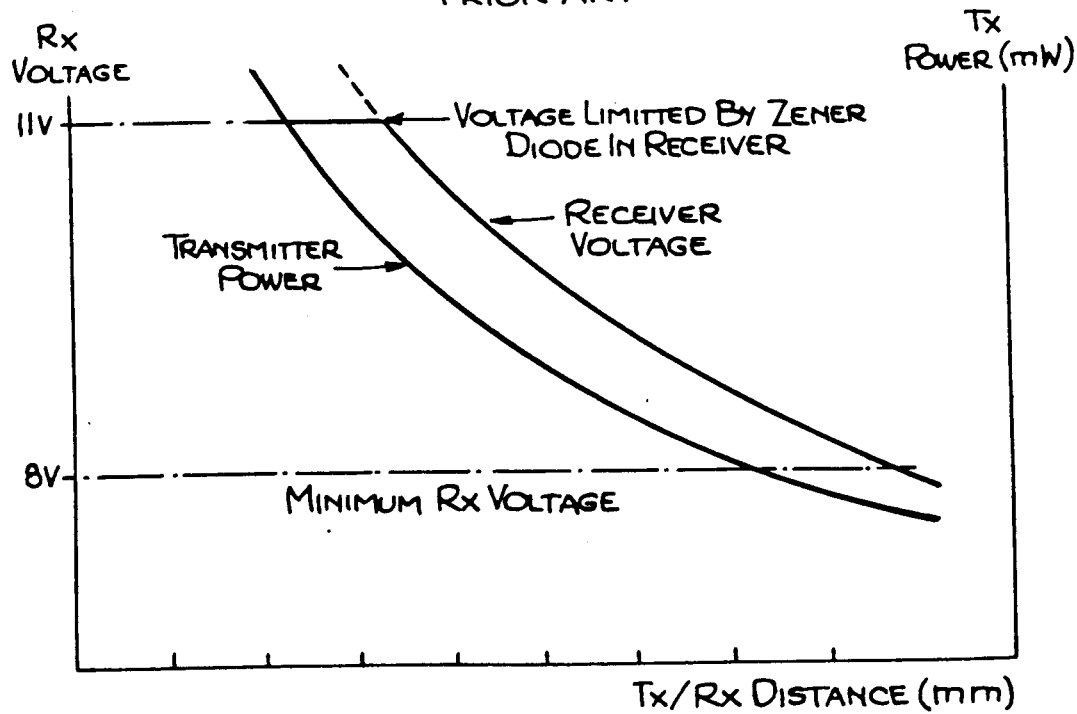
FIG. 3 is a graph of the coupling performance of a prior art five wire transmission system.

The RF signal at point A drives the transmitter resonant circuit including capacitor 45 and inductor 46. Capacitor 50 has a low impedance at 2.5 MHz and thus provides a ground return for the transmitter resonant circuit. Series coupling capacitor 42 couples the output of the class-E stage to the parallel tuned transmitter coil 46. When transmitter coil 46 is uncoupled from a receiver coil 80, which is electrically connected to an electronics package 82 associated with a cochlear implant under the skin 84 of a patient, the parallel tuned circuit presents a high impedance in series with capacitor 42, thus minimizing the detuning effect on the class-E stage. While a complex relationship may be derived for determining the optimum choice of values for capacitor 38 and capacitor 42, as a practical matter, capacitor 38 is tuned for minimum transmitter power at maximum coupling (i.e., minimum range) and the value of capacitor 42 is selected to provide sufficient power transfer at minimum coupling (i.e., maximum range). This means that the class-E circuit is optimally tuned, i.e. operating most efficiently, when the load reflected across the transmitter circuit is a maximum. As the reflected impedance increases, the voltage developed across the transmitter coil increases, thus compensating for the decreasing coupling coefficient and resulting in a more constant voltage being maintained at the receiver as illustrated in FIG. 5. This is an ideal power versus operating distance characteristic whereby the transmitter power is reduced as the receiver becomes more closely coupled.

It will be recognized that the coupling between the transmitter and receiver coils may be reduced not only by increasing the distance therebetween, but also by axial misalignment of the coils. Thus, "maximum range" may occur due to a greater distance between the coils or to misalignment. "Minimum range" occurs when the coils are coaxially aligned and at the closest possible distance apart. The distance is determined by the depth of the receiving coil below the skin, skin thickness, and headset design. For the latter, this is the distance between the plane of the transmitter coil and the skin.

Although the invention has been described with respect to particular embodiments, it is to be understood that these embodiments are merely illustrative of the application of the principles of the invention. Numerous modifications may be made therein and other arrangements may be devised without departing from the spirit and scope of the invention.

What is claimed is:

1. A three wire cabling system for transmitting audio and radio frequency energy comprising:
   (a) a three wire unshielded cable;
   (b) a radio frequency source connected to a first wire and a second wire of said three wire cable;
   (c) an audio frequency source connected to said second wire and a third wire of said three wire cable;
   (d) filter means coupled to said second and third wires of said cable for filtering audio from said audio frequency source to reduce interference from said radio frequency source;
   (e) implantable means for inserting in a patient's ear, said implantable means reflecting an impedance to said radio frequency source;
   (f) a radio frequency transmitter coil connected to said first wire and said second wire for receiving signals from said radio frequency source and for electromagnetically coupling said received signals at a selected output power level to said implantable means, said radio frequency means automatically adjusting its selected output power level in response to variations in said reflected impedance so that a substantially constant amount of power is electromagnetically coupled to said implantable device.

2. The three wire cabling system of claim 1, wherein radio frequency energy from said radio frequency source is wide band and comprises signal components in the audio frequency range.

3. A three wire cabling system for transmitting audio and radio frequency energy comprising:
   (a) a three wire unshielded cable;
   (b) a radio frequency source connected to a first wire and a second wire of said three wire cable;
   (c) an audio frequency source connected to said second wire and a third wire of said three wire cable, the radio frequency energy from said radio frequency source being at a voltage level several orders of magnitude higher than the voltage of said audio frequency source;
   (d) filter means coupled to said cable for filtering audio from said audio frequency source to reduce interference from said radio frequency source;
   (e) implantable means for inserting in a patient's ear, said implantable means reflecting an impedance to said radio frequency source; and
   (f) a radio frequency transmitter coil connected to said first wire and said second wire, for receiving signals from said radio frequency source and for electromagnetically coupling said received signals at a selected output power level to said implantable means, said radio frequency means automatically adjusting its selected output power level in response to variations in said reflected impedance so that a substantially constant amount of power is electromagnetically coupled to said implantable device.

4. The three wire cabling system of claim 3, wherein radio frequency energy from said radio frequency source is at a voltage level of substantially four orders of magnitude higher than voltage of said audio frequency source.

5. The three wide cabling system of claim 3, wherein said filter means is connected to said second wire and said third wire.

6. The three wire cabling system of claim 5, wherein said filter means includes at least one pi network.

7. The three wire cabling system of claim 1, wherein said filter means is coupled to said cable at least one end thereof.

8. A three wire cabling system for a cochlear implant speech processor comprising:
   a three wire unshielded cable having a first end and a second end;
   a radio frequency transmitter circuit connected to a first wire and a second wire of said three wire cable at the first end thereof;
   a radio frequency transmitter coil coupled to said first wire and said wire of said three wire cable at the second end thereof;
   an audio frequency source coupled to said second wire and a third wire of said three wire cable at said second end;
   an audio frequency processing means, for processing audio from said audio frequency source, coupled to said second wire and said third wire at said first end of said cable;
   filter means coupled to said second and third wires of said cable for filtering said audio so that it is substantially free of energy from said radio frequency transmitter circuit;
   implantable means for inserting in a patient's ear, said implantable means reflecting an impedance to said radio frequency source; and
   a radio frequency transmitter coil connected to said first wire and said second wire, for receiving signals from said radio frequency source and for electromagnetically coupling said received signals at a selected output power level to said implantable means, said radio frequency means automatically adjusting its selected output power level in response to variations in said reflected impedance so that a substantially constant amount of power is electromagnetically coupled to said implantable device.

9. The three wire cabling system of claim 8, wherein said audio source is a microphone for receiving ambient audio, and said transmitter coil and said microphone are located proximate one another.

10. A transmission system for a cochlear implant speech processor comprising:
    a three wire unshielded cable having a first end and a second end;
    a radio frequency transmitter circuit connected to a first wire and a second wire of said three wire cable at the first end thereof;
    a radio frequency transmitter coil coupled to said first wire and said second wire of said three wire cable at the second end thereof;
    an audio frequency source coupled to said second wire and a third wire of said three wire cable at said second end;
    an audio frequency processing means, for processing audio from said audio frequency source, coupled to said second wire and said third wire at said first end of said cable;
    filter means for filtering said audio so that it is substantially free of energy from said radio frequency transmitter circuit;

pulsing means for pulsing said radio frequency transmitter circuit to produce pulsed radio frequency output;

implantable means for inserting in a patient's ear, said implantable means reflecting an impedance to said radio frequency source; and a radio frequency transmitter coil connected to said first wire and said second wire, for receiving signals from said radio frequency source and for electromagnetically coupling said received signals at a selected output power level to said implantable means, said radio frequency means automatically adjusting its selected output power level in response to variations in said reflected impedance so that a substantially constant amount of power is electromagnetically coupled to said implantable device.

11. A transmission system for a cochlear implant speech processor comprising:

a three wire unshielded cable having a first end and a second end;

a radio frequency transmitter circuit connected to a first wire and a second wire of said three wire cable at the first end thereof;

a radio frequency transmitter coil coupled to said first wire and said second wire of said three wire cable at the second end thereof;

an audio frequency source coupled to said second wire and a third wire of said three wire cable at said second end;

an audio frequency processing means, for processing audio from said audio frequency source, coupled to said second wire and said third wire at said first end of said cable;

filter means for filtering said audio so that it is substantially free of energy from said radio frequency transmitter circuit, said first means including a filter at least one end of said cable;

implantable means for inserting in a patient's ear, said implantable means reflecting an impedance to said radio frequency source; and a radio frequency transmitter coil connected to said first wire and said second wire, for receiving signals from said radio frequency source and for electromagnetically coupling said received signals at a selected output power level to said implantable means, said radio frequency means automatically adjusting its selected output power level in response to variations in said reflected impedance so that a substantially constant amount of power is electromagnetically coupled to said implantable device.

12. The transmission system of claim 11, wherein said filter is a pi network.

13. The transmission system of claim 10, wherein said filter means is connected to said second wire and said third wire.

14. The transmission system of claim 13, wherein said filter means is a pi network.

15. A radio frequency transmission system for a cochlear implant comprising:

a transmitter having a first tuned circuit, said first tuned circuit including a coil having a tap, said tap and one side of said coil being connected to a radio frequency driver including at least one active device;

a transmitter coil which is part of a second tuned circuit, and coupling means for coupling radio frequency energy from said first tuned circuit to said second tuned circuit, said coupling means including a capacitor, one side of said capacitor being connected to another side of said tapped coil, and another side of said capacitor being connected to said transmitter coil of said second tuned circuit.

16. The radio frequency transmission system of claim 15, further comprising a receiving coil coupled to said transmitter coil; wherein said first tuned circuit has component values adjusted for resonance at a minimum range between said transmitter coil and said receiving coil, and said coupling means has a value which assures a predetermined energy transfer between said transmitter coil and said receiving coil at a maximum range between said transmitter coil and said receiving coil.

* * * * *